United States Patent
Alsaffar et al.

(10) Patent No.: US 11,766,288 B2
(45) Date of Patent: Sep. 26, 2023

(54) FLEXIBLE BIPOLAR SHEATH

(71) Applicant: Gyrus ACMI, Inc., Southborough, MA (US)

(72) Inventors: Ahmad Alsaffar, Bartlett, TN (US); Joel Willhite, Memphis, TN (US)

(73) Assignee: Gyrus ACMI, Inc., Westborough, MA (US)

( * ) Notice: Subject to any disclaimer, the term of this patent is extended or adjusted under 35 U.S.C. 154(b) by 728 days.

(21) Appl. No.: 16/282,760

(22) Filed: Feb. 22, 2019

(65) Prior Publication Data

US 2020/0268435 A1 Aug. 27, 2020

(51) Int. Cl.
 *A61B 18/14* (2006.01)
 *A61B 17/3207* (2006.01)
 (Continued)

(52) U.S. Cl.
 CPC ...... *A61B 18/14* (2013.01); *A61B 17/320708* (2013.01); *A61B 18/1206* (2013.01);
 (Continued)

(58) Field of Classification Search
 CPC ............ A61B 18/14; A61B 17/320708; A61B 18/1206; A61B 2018/00083; A61B 2018/00172; A61B 2018/00178; A61B 2018/00589; A61B 2018/00982; A61B 2018/126; A61B 2018/1412; A61B 2018/00184; A61B 2018/00601; A61B 2018/1495; A61B 18/1492; A61B 18/082; A61B 2017/320082; A61B 2017/320075; A61B 2017/320077; A61B 2017/320074; A61B 2018/00607; A61B 2018/00577; A61B 2017/32007; A61B 2017/320069; A61B 17/320016; A61B 17/32002; A61B 2017/320024; A61B 2017/320028;
 (Continued)

(56) References Cited

U.S. PATENT DOCUMENTS

| 3,054,464 A | 9/1962 | Ondeck |
| 3,201,670 A | 8/1965 | Myers |

(Continued)

FOREIGN PATENT DOCUMENTS

| EP | 3698746 A1 | 8/2020 |
| EP | 3721824 A1 | 10/2020 |

(Continued)

OTHER PUBLICATIONS

"U.S. Appl. No. 16/365,735, Non Final Office Action dated Oct. 20, 2021", 12 pgs.

(Continued)

*Primary Examiner* — Linda C Dvorak
*Assistant Examiner* — Mystee Nguyen Delgado
(74) *Attorney, Agent, or Firm* — Schwegman Lundberg & Woessner, P.A.

(57) ABSTRACT

A medical instrument sheath including an elongated hollow tube having a wall comprised of polymeric material; and at least one electrical lead embedded inside the wall, wherein the at least one electrical lead is configured to be connected with a respective electrode disposed in a member located inside the sheath and extending from a distal end of the sheath.

14 Claims, 6 Drawing Sheets

(51) Int. Cl.
*A61B 18/12* (2006.01)
*A61B 17/00* (2006.01)
*A61B 18/00* (2006.01)

(52) U.S. Cl.
CPC ............ *A61B 2017/00526* (2013.01); *A61B 2018/00083* (2013.01); *A61B 2018/00172* (2013.01); *A61B 2018/00178* (2013.01); *A61B 2018/00589* (2013.01); *A61B 2018/00982* (2013.01); *A61B 2018/126* (2013.01); *A61B 2018/1412* (2013.01)

(58) Field of Classification Search
CPC .......... A61B 17/32; A61B 2018/00196; A61B 2018/00202; A61B 2018/00208
See application file for complete search history.

(56) References Cited

U.S. PATENT DOCUMENTS

| | | | |
|---|---|---|---|
| 5,364,395 A * | 11/1994 | West, Jr. | .......... A61B 17/32002 606/49 |
| 6,190,385 B1 | 2/2001 | Tom et al. | |
| 6,193,715 B1 * | 2/2001 | Wrublewski | ....... A61B 18/1402 606/49 |
| 6,258,111 B1 | 7/2001 | Ross et al. | |
| 6,293,957 B1 | 9/2001 | Peters et al. | |
| 7,150,747 B1 | 12/2006 | Mcdonald et al. | |
| 7,174,220 B1 * | 2/2007 | Chitre | .................... A61N 1/056 600/374 |
| 7,226,459 B2 | 6/2007 | Cesarini et al. | |
| 7,510,563 B2 | 3/2009 | Cesarini et al. | |
| 7,666,200 B2 | 2/2010 | Heisler | |
| 7,669,209 B2 | 2/2010 | Inohara et al. | |
| 7,669,309 B2 | 3/2010 | Johnson et al. | |
| 8,286,899 B2 | 10/2012 | Schowalter et al. | |
| 9,078,664 B2 * | 7/2015 | Palmer | ................. A61B 18/148 |
| 9,446,229 B2 | 9/2016 | Omar-Pasha | |
| 9,895,191 B2 | 2/2018 | Conley et al. | |
| 9,949,792 B2 | 4/2018 | Paul et al. | |
| 10,159,523 B2 | 12/2018 | Sartor et al. | |
| 10,188,456 B2 | 1/2019 | Prisco et al. | |
| 10,342,572 B2 | 7/2019 | Govari et al. | |
| 10,582,966 B2 | 3/2020 | Orczy-timko et al. | |
| 2006/0200123 A1 * | 9/2006 | Ryan | .................... A61B 18/148 606/48 |
| 2007/0250055 A1 * | 10/2007 | Johnson | ................ A61N 1/0551 606/41 |
| 2008/0125754 A1 * | 5/2008 | Beer | ........................ A61L 29/14 427/2.24 |
| 2008/0208233 A1 | 8/2008 | Barnes | |
| 2009/0012512 A1 * | 1/2009 | Utley | .................. A61B 18/1492 606/34 |
| 2010/0049191 A1 * | 2/2010 | Habib | ................ A61B 18/1492 606/41 |
| 2013/0331833 A1 | 12/2013 | Bloom | |
| 2013/0345704 A1 * | 12/2013 | Palmer | ................. A61B 18/148 606/41 |
| 2014/0100567 A1 | 4/2014 | Edwards et al. | |
| 2015/0173825 A1 * | 6/2015 | Bloom | ............. A61B 17/32002 606/50 |
| 2015/0327880 A1 | 11/2015 | Wasicek et al. | |
| 2015/0351826 A1 * | 12/2015 | Kroeber | ............. A61B 1/00124 600/105 |
| 2016/0235474 A1 * | 8/2016 | Prisco | ............. A61B 17/32002 |
| 2016/0361084 A1 | 12/2016 | Weisenburgh, II et al. | |
| 2017/0049514 A1 | 2/2017 | Cosman | |
| 2017/0143406 A1 | 5/2017 | Bloom | |
| 2017/0215955 A1 | 8/2017 | Hancock et al. | |
| 2017/0303986 A1 | 10/2017 | Hancock et al. | |
| 2017/0360497 A1 | 12/2017 | Hancock et al. | |
| 2018/0116711 A1 * | 5/2018 | Suh | .................. A61B 17/32002 |
| 2019/0059983 A1 | 2/2019 | Germain et al. | |
| 2019/0231378 A1 | 8/2019 | Church et al. | |
| 2019/0321063 A1 | 10/2019 | Germain et al. | |
| 2020/0323582 A1 | 10/2020 | Willhite et al. | |

FOREIGN PATENT DOCUMENTS

| | | | | |
|---|---|---|---|---|
| JP | H08155031 A | 6/1996 | | |
| JP | 2014534874 A | 12/2014 | | |
| JP | 2015519147 A | 7/2015 | | |
| JP | 2017531514 A | 10/2017 | | |
| JP | 2018504983 A | 2/2018 | | |
| JP | 2020131042 A | 8/2020 | | |
| JP | 7231580 B2 | 2/2023 | | |
| WO | WO-2016132340 A1 | 0/8201 | | |
| WO | WO-0033753 A1 * | 6/2000 | ............. A61B 18/14 | |
| WO | WO-0056238 A1 * | 9/2000 | ......... A61B 18/1402 | |
| WO | WO-2008153357 A2 | 12/2008 | | |
| WO | WO-2014055131 A1 | 4/2014 | | |
| WO | WO-2015061643 A2 | 4/2015 | | |
| WO | WO-2015/116692 A1 | 8/2015 | | |
| WO | WO-2016059228 A2 | 4/2016 | | |
| WO | WO-2016134156 A1 | 8/2016 | | |
| WO | WO-2017103209 A1 | 6/2017 | | |
| WO | WO-2019034710 A1 | 2/2019 | | |

OTHER PUBLICATIONS

"U.S. Appl. No. 16/365,735, Response filed Jan. 20, 2022 to Non Final Office Action dated Oct. 20, 2021", 12 pgs.

"ConMed", [Online], Retrieved from the Internet: <http://www.conmed.com/en/products/orthopedics/ablation/bipolarablation/edge-bipolar-mthroscopic-rf-system>, (Jan. 25, 2018), 2 pgs.

"Disposable Tonsil Adenoid Debrider", [Online], Retrieved from the Internet: <http://medical.olympusamerica.com/products/debrider/dtad-70 138400>, (Jan. 25, 2018), 1 pg.

"ESSx Microdebrider", [Online], Retrieved from the Internet: <https://nse.stryker.com/wp-content/uploads/2016/09/ESSx- Microdebrider-brochure.pdf>, (Jan. 25, 2018), 2 pgs.

"European Application Serial No. 20158849.8, Extended European Search Report dated Jul. 6, 2020", 11 pgs.

"European Application Serial No. 20158849.8, Response filed Feb. 24, 2021 to Extended European Search Report dated Jul. 6, 2020", 11 pgs.

"European Application Serial No. 20168120.2, Communication Pursuant to Article 94(3) EPC dated Jul. 26, 2021", 5 pgs.

"European Application Serial No. 20168120.2, Extended European Search Report dated Jul. 28, 2020", 8 pgs.

"European Application Serial No. 20168120.2, Response filed Apr. 12, 2021 to Extended European Search Report dated Jul. 28, 2020", 8 pgs.

"European Application Serial No. 20168120.2, Response filed Dec. 2, 2021 to Communication Pursuant to Article 94(3) EPC dated Jul. 26, 2021", 10 pgs.

"Hightlights 2017 Otorhinolaryngology", Edition Jan. 2017, [Online], Retrieved from the Internet: <https: //www.karlstorz.com/cps/rde/xbcr/karlstorz assets/ ASSETS/34824 34. pdf>, (Jan. 25, 2018), 20 pgs.

"Japanese Application Serial No. 2020-028554, Notification of Reasons for Rejection dated Mar. 22, 2021", w/ English Translation, 9 pgs.

"Japanese Application Serial No. 2020-071135, Final Notification of Reasons for Refusal dated Nov. 22, 2021", w/ English Translation, 5 pgs.

"Japanese Application Serial No. 2020-071135, Notification of Reasons for Refusal dated May 24, 2021", w/English Translation, 11 pgs.

"Japanese Application Serial No. 2020-071135, Response filed Aug. 13, 2021 to Notification of Reasons for Refusal dated May 24, 2021", with machine translation, 10 pgs.

"Multidebrider Diego Elite", <http://medical.olympusamerica.com/products/debrider/diego%C2%AE-elite>, (Jan. 25, 2018), 2 pgs.

"PolypVac", [Online], Retrieved from the Internet: <https://zcl.campaignview.com/ua/viewinbrowser?od=11287eca5dbc3b&rd=

(56) References Cited

OTHER PUBLICATIONS

119f933bb603779b&sd=119f933bb6033495&n=11699e4beebbffe&mrd=119f933bb6033487&m=1 >, (Jul. 20, 2017), 2 pgs.
"Smith & Nephew", [Online], Retrieved from the Internet: <http://www.smith-nephew.com/professional/products/allproducts/dyonics-power-ii-control-system>, (Jan. 25, 2018), 2 pgs.
"Straightshot M4 Microdebrider", [Online], Retrieved from the Internet: http://www.medtronic.com/us-en/healthcare-professionals/products/ear-nose-throat/powered-ent-instruments/powered-ent-instruments/handpieces-accessories.html, (Jan. 25, 2018), 1 pg.
"Straightshot M5 Microdebrider", [Online], Retrieved from the Internet: <http://www.medtronic.com/for-healthcareprofessionals/business-unit-landing-Page/straightshot-m5-30k-burs/index.htm>, (Jan. 25, 2018), 1 pg.
"THUNDERBEAT Generators", [Online], Retrieved from the Internet: <http://medical.olympusamerica.com/products/thunderbeat-generators-esg-400-usg-400>, (Jan. 25, 2018), 2 pgs.
"U.S. Appl. No. 16/365,735, Final Office Action dated Feb. 14, 2022", 15 pgs.
U.S. Appl. No. 16/365,735, filed Apr. 11, 2019, Medical Device.
"Japanese Application Serial No. 2020-028554, Response filed Jun. 21, 2021 to Notification of Reasons for Rejection dated Mar. 22, 2021", w/ English Claims, 10 pgs.
"Japanese Application Serial No. 2020-28554, Examiners Decision of Final Refusal dated Sep. 21, 2021", w/ English Translation, 5 pgs.
"U.S. Appl. No. 16/365,735, Non Final Office Action dated Jun. 13, 2022", 15 pgs.
"U.S. Appl. No. 16/365,735, Response filed Apr. 14, 2022 to Final Office Action dated Feb. 14, 2022", 12 pgs.
"European Application Serial No. 20168120.2, Communication Pursuant to Article 94(3) EPC dated May 31, 2022", 5 pgs.
"Japanese Application Serial No. 2020-071135, Response filed Feb. 16, 2022 to Final Notification of Reasons for Refusal dated Nov. 22, 2021", w/English translation, 4 pgs.
"U.S. Appl. No. 16/365,735, Examiner Interview Summary dated Sep. 20, 2022", 2 pgs.
"U.S. Appl. No. 16/365,735, Response filed Sep. 13, 2022 to Non Final Office Action dated Jun. 13, 2022", 15 pgs.
"European Application Serial No. 20168120.2, Response filed Aug. 2, 2022 to Communication Pursuant to Article 94(3) EPC dated May 31, 2022", w/ English claims, 56 pgs.
"Japanese Application Serial No. 2020-71135, Notification of Reasons for Refusal dated Jul. 4, 2022", w/ English translation, 5 pgs.
"U.S. Appl. No. 16/365,735, Advisory Action dated May 2, 2022", 3 pgs.
"Japanese Application Serial No. 2020-71135, Response filed Oct. 4, 2022 to Notification of Reasons for Refusal dated Jul. 4, 2022", with machine translation, 9 pgs.
"U.S. Appl. No. 16/365,735, Notice of Allowance dated Mar. 3, 2023", 8 pgs.
"U.S. Appl. No. 16/365,735, Response filed Feb. 14, 2023 to Final Office Action dated Jan. 13, 2023", 13 pgs.
"U.S. Appl. No. 16/365,735, Final Office Action dated Jan. 13, 2023", 14 pgs.
"European Application Serial No. 20158849.8, Communication Pursuant to Article 94(3) EPC dated Apr. 5, 2023", 6 pgs.

* cited by examiner

FLEXIBLE BIPOLAR SHEATH

BACKGROUND

Technical Field

The example and non-limiting embodiments relate generally to a sheath for an endoscope and, more particularly, to a flexible bipolar sheath.

Brief Description of Prior Developments

Monopolar electrodes and bipolar electrodes have been known to be provided on catheters, sheathes, shavers, and debriders. Examples of bipolar devices are shown in U.S. Pat. Nos. 9,895,191 and 6,193,715 for example which are hereby incorporated by reference in their entireties.

SUMMARY

The following summary is merely intended to be exemplary. The summary is not intended to limit the scope of the claims.

In accordance with one aspect, an example embodiment is provided in a sheath comprising an elongated hollow tube having a wall comprised of polymeric material; and at least one electrical lead embedded inside the wall, wherein the at least one electrical lead is configured to be connected with a respective electrode disposed in a member located inside the sheath and extending from a distal end of the sheath.

In accordance with another aspect, an example embodiment is provided in a medical device comprising a polymeric sheath; and at least one electrode disposed in a member separate from the polymeric sheath, wherein the polymeric sheath and the at least one electrode are configured to provide radiofrequency (RF) energy for a surgical operation when the polymeric sheath is connected to an radiofrequency (RF) energy source.

In accordance with another aspect, an example method of manufacturing a sheath comprises extruding a tube of polymeric material; embedding at least one electrode in a wall of the tube as the tube is being extruded; and exposing opposite ends of the at least one electrode to allow the opposite ends to be electrically connected to different members.

BRIEF DESCRIPTION OF THE DRAWINGS

The foregoing aspects and other features are explained in the following description, taken in connection with the accompanying drawings, wherein.

DETAILED DESCRIPTION OF EMBODIMENTS

Figure 1:
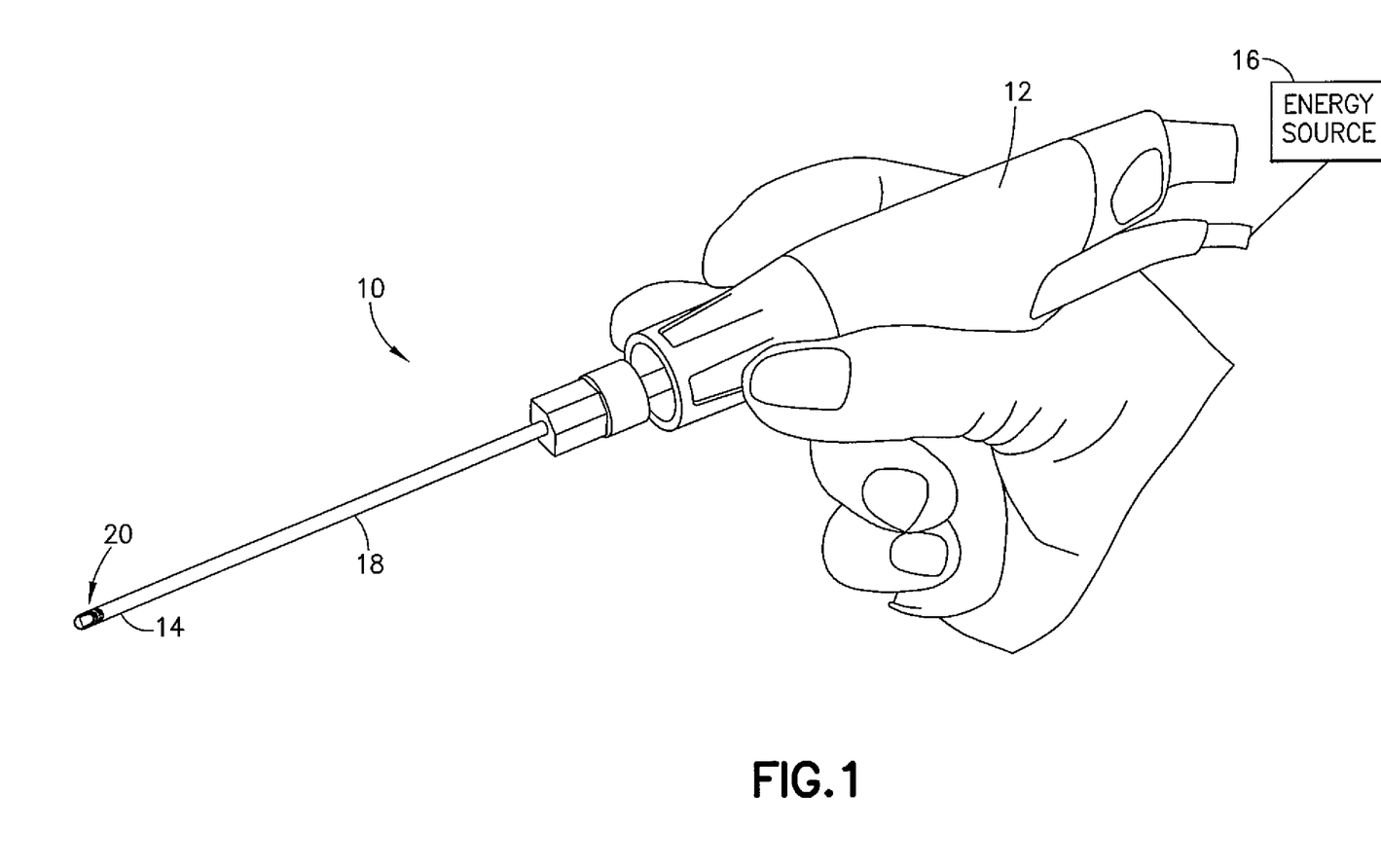
FIG. 1 is a schematic perspective view of an example embodiment.

Referring to FIG. 1, there is shown a schematic view of an apparatus 10 incorporating features of an example embodiment. Although the features will be described with reference to the example embodiments shown in the drawings, it should be understood that features can be embodied in many alternate forms of embodiments. In addition, any suitable size, shape or type of elements or materials could be used.

The apparatus 10 is a microdebrider in this example. However, features as described herein may be used with any suitable medical instrument having a sheath. A microdebrider is an instrument that has a hollow tube with an inner and outer portion. At a distal end of the tube, both inner and outer portions of the tube have a blade that cuts tissue as the blades either moved back and forth relative to each other or as an inner blade is rotated relative to an outer blade. The tube forms a catheter which can have continuous suction applied so that cut tissue is capture and removed from the surgical area. In the example shown, the apparatus 10 has a handle 12 and a forward extending portion 14. The apparatus 10 may be connected to an energy source 16 for bipolar coagulation for example, as well as a source of vacuum and perhaps a visual imaging system.

Figure 2:
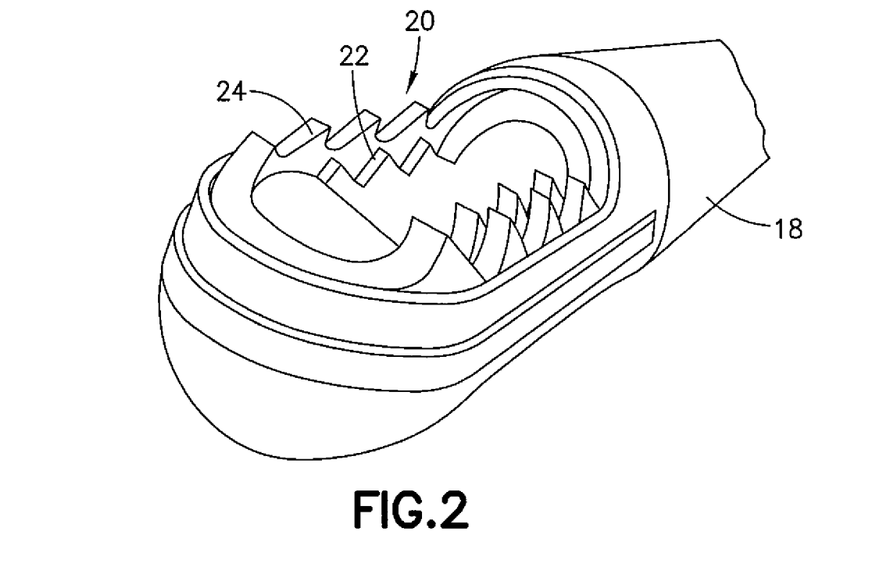
FIG. 2 is a perspective view of the distal end of the apparatus shown in FIG. 1.

Referring also to FIG. 2, the forward extending portion 14 forms a shaft which may be inserted into a patient. The shaft 14 comprises an outer sheath 18 and a bipolar blade assembly 20 which are configured for both debriding as well as bipolar coagulation. FIG. 2 shows the distal tip of the shaft 14. The blade assembly 20 comprises an inner blade 22 and an outer blade 24. The inner blade 22 is able to be moved relative to the outer blade 24 by a driver in the handle 12. The relative motion of the blades 22, 24 allows tissue to be cut, and the cut tissue may be evacuated through a channel in the inner blade 22.

Figure 3:
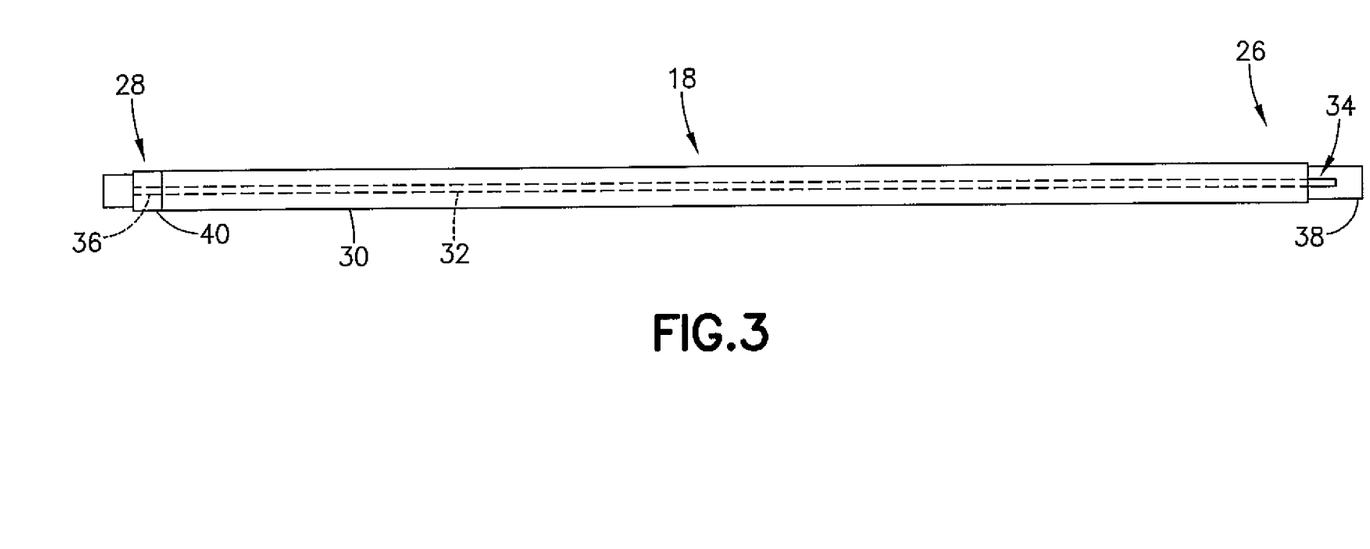
FIG. 3 is a side view of the outer sheath shown in FIGS. 1-2.
Figures 4, 5:
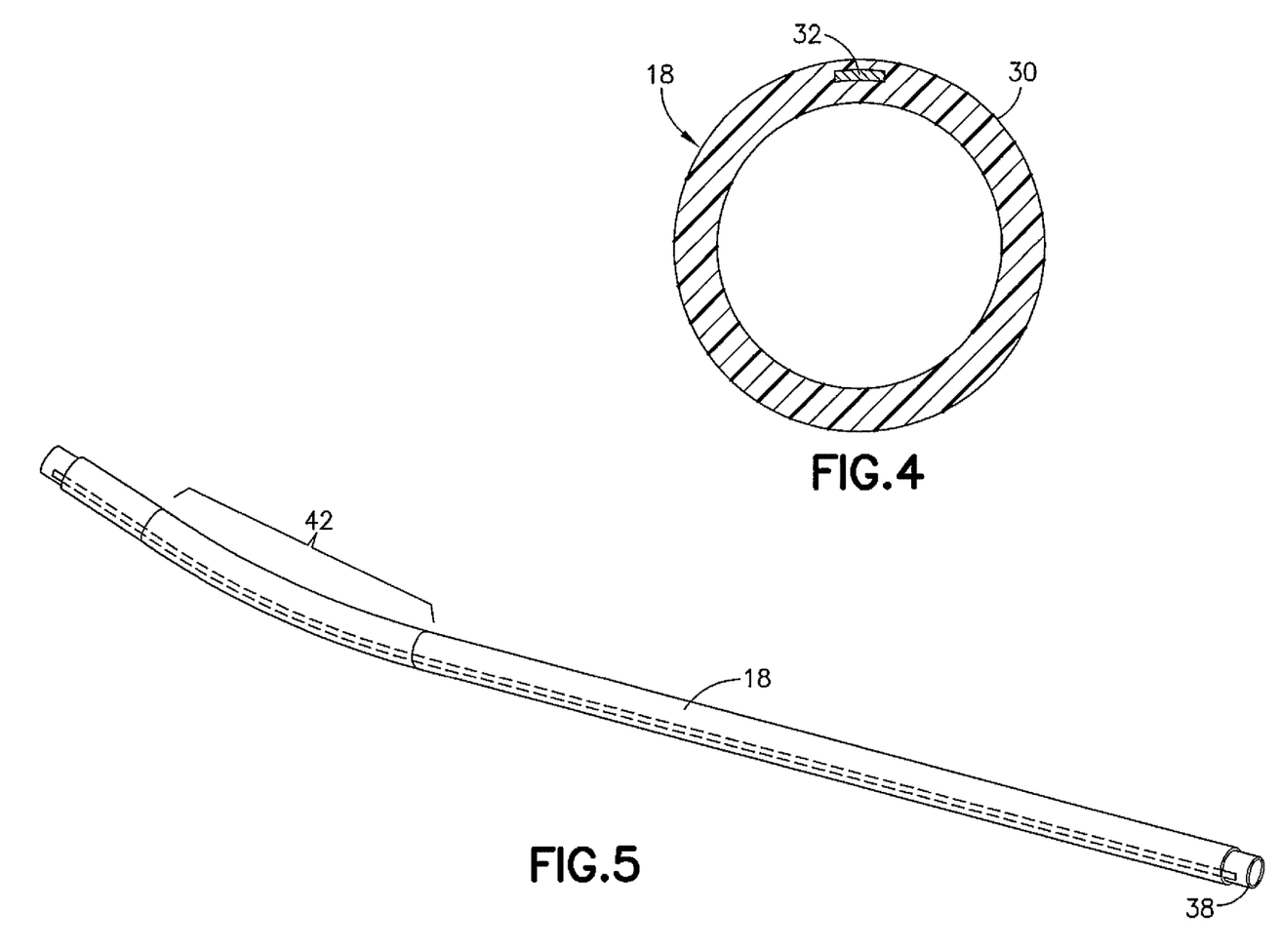
FIG. 4 is a cross sectional view of the sheath shown in FIG. 3.
FIG. 5 is a side view of the sheath shown in FIG. 3 showing a bend in the sheath.

Referring also to FIGS. 3-4, the outer sheath 18 has a proximal end 26 and a distal end 28. The outer sheath 18 comprises a tube 30 of polymeric material and an electrical conductor 32. In this example the electrical conductor 32 is embedded inside a wall of the tube 30. The electrical conductor 32 extends the entire length of the tube 30 and opposite ends 34, 36 of the electrical conductor 32 extend out of the proximal and distal ends 26, 28 of the tube 30. In FIG. 3 the outer sheath 18 is shown on a support frame 38. However the support frame might not be provided. In an example method of manufacturing the sheath 18, the tube 30 may be extruded with the conductor 32 embedded in the wall during the extrusion process. Thus, the tube 30 may function as an electrical insulator for the conductor 32, but the exposed ends 34, 36 allow for electrical connection of the conductor 32 to other members. In an alternate example, a different method other than embedding during extrusion may be provided to connect the conductor 32 with the tube 30.

Figures 6, 7:
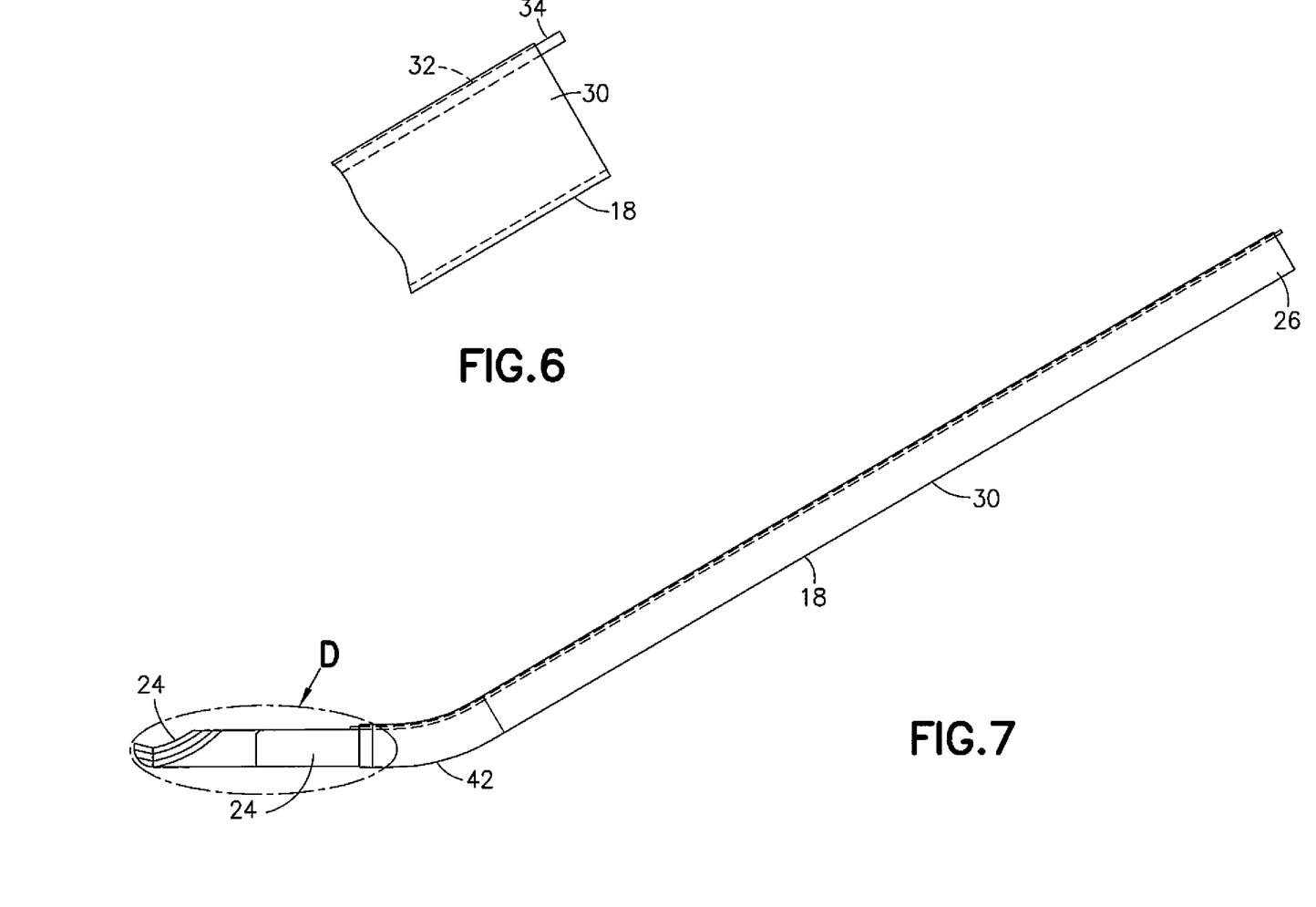
FIG. 6 is a partial side view of the proximal end of the sheath shown in FIGS. 3-5.
FIG. 7 is a side view of an embodiment of the shaft shown in FIG. 1.
Figure 8:
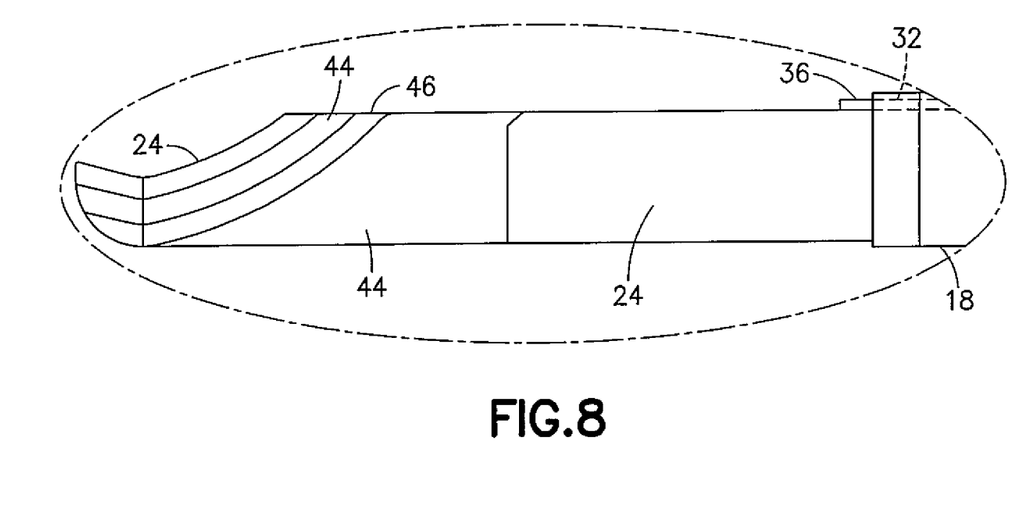
FIG. 8 is an enlarged view of area D in FIG. 7.
Figure 9:
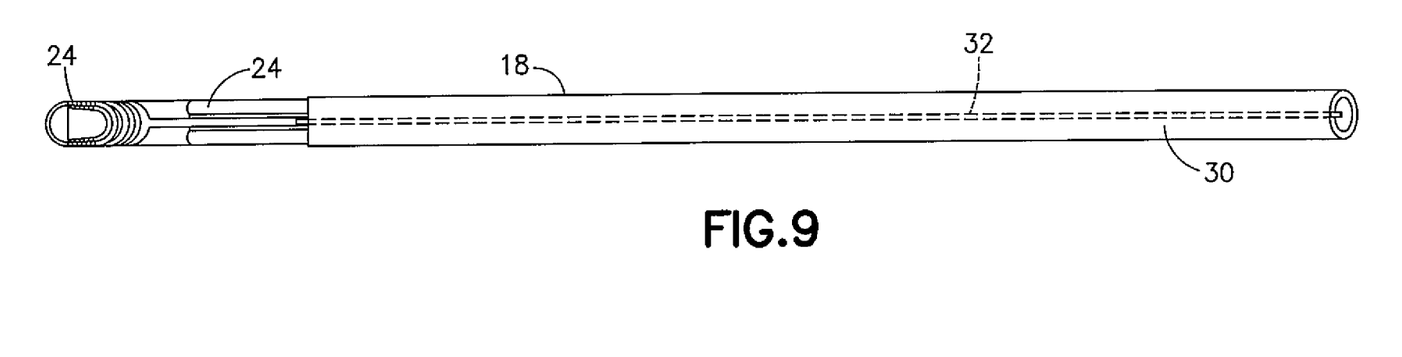
FIG. 9 is a top view of the shaft shown in FIGS. 7-8.
Figure 10:
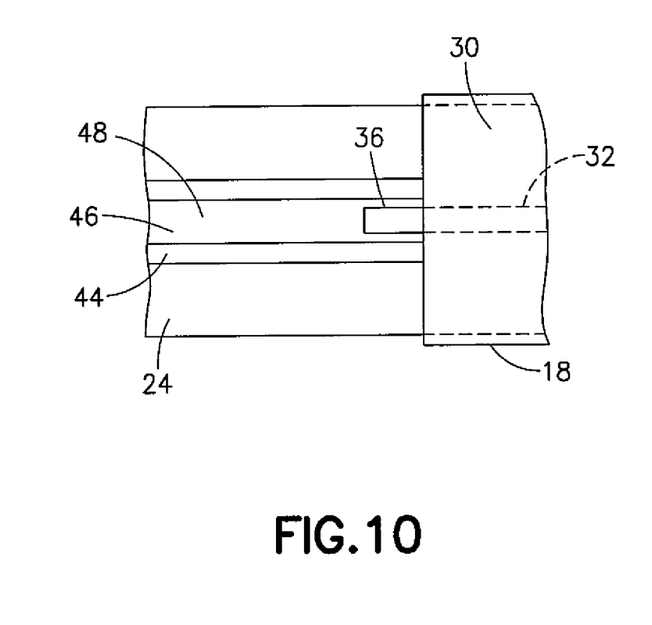
FIG. 10 is a partial top view of the distal end of the sheath and blade shown in FIG. 9.

As seen in FIG. 6, the end 34 of the electrical conductor 32 extends out from the proximal end of the tube 30. Thus, the end 34 may be mechanically an electrical connected to another member, such as a conductor from the energy source 16. FIG. 3 shows and example of an electrical insulator 40 which may be placed over the end 36 to electrically insulate the end 36 after connection to another member. Referring also to FIG. 5, the combined support frame 38 and outer sheath 18 may have a flexible section 42. This provides a flexible/semi-rigid sheath assembly.

Referring also to FIGS. 7-10, an example embodiment is shown where the outer blade 24 forms the support frame 38. The outer sheath 18 is located directly on the outer blade 24 and the material of the tube 30 electrically insulates the outer blade 24 from the electrical conductor 32. The outer blade 24 extends through the outer sheath 30 and out the distal end of the outer sheath. As seen best in FIGS. 8 and 10, an electrical insulator 44 is provided on the outer blade 24 at its distal end. An electrical conductor 46 is located on the electrical insulator 44. The electrical conductor 46, in this example, extends around the opening of the outer blade 24 at the distal tip as a general loop and has a leg 48 which extends towards the outer sheath 18. The distal end 36 of the electrical conductor 32 is connected to the leg 48 of the electrical conductor 46. One or more bipolar traces are laid out at the tip of the blade 24 and, in this example the electrical conductor 46 forms on of the bipolar traces. The electrical return may be the metal blade itself 24. Thus, the electrical conductors 32 connected to the trade 46 may be used for coagulation at the distal end of the shaft 14 via the trace 46 and the metal blade 24 itself. Other configurations, such as when the blade 24 is not the electrical return for example, could have two metal strips inside the sheath and two traces at the distal tip.

A conventional microdebrider utilizes a stainless steel sheath, separated from an outer blade by an electrically insulative coating of halar, and covered with insulative shrink tubing to achieve a desired electrode placement at the tip of the blade. With features as described herein, one or more bipolar electrodes may be connected with a flexible/semi-rigid sheath having one or more integrated conductive pathways that allow for the connection to an energy source farther proximal to the tip. Extra insulation is not required because of the inherent insulation property of the tube of the sheath. This may allow current curved microdebrider blades to utilize bipolar energy which is currently not offered. With features as described herein, the shaft 14 may be manufactured less expensive than conventional existing debrider shafts. With features as described herein, the shaft 14 may have less components than conventional existing debrider shafts. With features as described herein, the outer sheath 18 is electrically self-insulating. With features as described herein, a curved/bendable/malleable bipolar microdebrider blade assembly may be provided.

Figure 11:
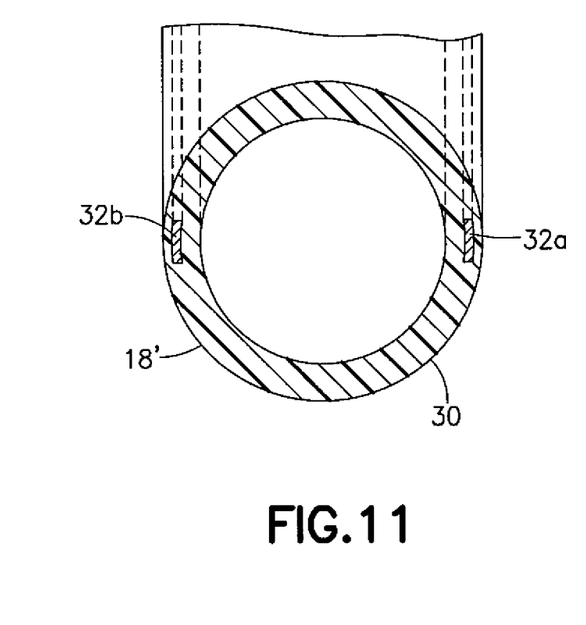
FIG. 11 is a schematic cross sectional view of an alternate example embodiment of the outer sheath.

Referring also to FIG. 11, an alternate example is shown. In this example the outer sheath 18' has two electrical conductors 32a, 32b embedded in the tube 30. The tube 30 may be extruded onto the conductors 32a, 32b for example. The conductors 32a, 32b are located on opposite sides of the tube in this example. Each conductor 32a, 32b has an exposed proximal end which extends from the proximal end of the tube and an exposed distal end which extends from a distal end of the tube. This would allow both electrodes of the bipolar configuration to be electrically connected through the outer sheath's electrical conductors.

With an example embodiment, the end 34 of the electrical conductor 32 may function as a bipolar lead to be connected to an energy sources as a bipolar energy source. The electrical conductor 32 functions as a bipolar lead insulated from the blade 24 by the material of the tube 30. The end 36 of the electrical conductor forms a bipolar lead for termination to a bipolar trace on the outer blade 24, and the connection of the end 36 to the trace may be covered by electrical insulation 40 such as a shrink tube for example.

The exposed strip 36 may be soldered directly to the bipolar trace 46. Alternatively, it could be connected via epoxy or mechanical connection. This connection joint could be covered with shrink tubing. The flexible shaft allows the blade 24 and lead 32 to be bent. The lead 32 may be a thin metal this is extruded with the flexible shaft. An example embodiment provides a flexible sheath with at least one embedded strip of conductive metal. The strip of metal extends past the sheath at both ends.

An example embodiment may be provided in a polymeric sheath comprising: an elongated hollow tube having a wall; and one or more electrical (metallic) leads embedded inside the wall, wherein the one or more conductive paths are configured to be physically in connection with one or more electrodes disposed in a member separate from the polymeric sheath.

An example embodiment may be provided in a medical device comprising: a polymeric sheath; and one or more electrodes disposed in a member separate from the polymeric sheath, wherein the polymeric sheath and the one or more electrodes are configured to provide RF energy for a surgical operation when the polymeric sheath is connected to a RF source. The polymeric sheath may comprise one or more electrical leads.

In accordance with one example embodiment, a medical instrument sheath is provided comprising: an elongated hollow tube having a wall comprised of polymeric material; and at least one electrical lead embedded inside the wall, wherein the at least one electrical lead is configured to be connected with a respective electrode disposed in a member located inside the sheath and extending from a distal end of the sheath.

The at least one electrical lead may comprise a single electrical lead along a length of the tube. The at least one electrical lead may comprise two of the electrical leads extending along a length of the tube. A distal portion of the sheath may be flexible in a semi-rigid fashion including the wall and the at least one electrical lead being bendable at the distal portion. The tube may comprise extruded onto the at least one electrical lead to from the at least one electrical lead embedded inside the wall. Opposite ends of the at least one electrical lead may be exposed at opposite ends of the tube. An apparatus may be provided comprising the sheath as described above and further comprising the member mechanically connected to a distal end of the tube, where the member comprises an electrically conductive member which is electrically connected to a distal end of the at least one electrical lead. The apparatus may further comprise an electrically insulating member located over a connection of the electrically conductive member to the distal end of the at least one electrical lead. The electrically conductive member may comprise a portion of a bipolar trace for bipolar coagulation. The member may be configured to have a distal end of a debrider blade, extending through the sheath, located therein.

In accordance with one example embodiment, a medical device may be provided comprising: a polymeric sheath; and at least one electrode disposed in a member separate from the polymeric sheath, wherein the polymeric sheath and the at least one electrode are configured to provide radiofrequency (RF) energy for a surgical operation when the polymeric sheath is connected to an radiofrequency (RF) energy source. The polymeric sheath comprises at least one electrical leads.

In accordance with an example method, a method may be provided for manufacturing a sheath comprising: extruding a tube of polymeric material; embedding at least one electrode in a wall of the tube as the tube is being extruded; and exposing opposite ends of the at least one electrode to allow the opposite ends to be electrically connected to different members.

The embedding of the at least one electrode in the wall of the tube as the tube is being extruded may comprise embedding a single electrode along a length of the wall. The method may further comprise connecting a member to a distal end of the sheath, where the member extends out of the distal end of the sheath, and where one of the ends of the single electrode is electrically connected to a bipolar conductor of the member for bipolar coagulation. The embedding of the at least one electrode in the wall of the tube as the tube is being extruded may comprise embedding a spaced pair of the electrodes along a length of the wall. The method may further comprise connecting a member to a distal end of the sheath, where the member extends out of the distal end of the sheath, and where first ones of the ends of the pair of electrodes are electrically connected to a pair of bipolar conductors of the member for bipolar coagulation. The method may further comprise connecting a member to a distal end of the sheath, where the member extends out of the distal end of the sheath, electrically connecting a bipolar coagulation conductor on the member to one of the ends of the at least one electrode, and inserting a debrider blade through the sheath, where a distal end of the debrider blade is located in a seat of the member.

It should be understood that the foregoing description is only illustrative. Various alternatives and modifications can be devised by those skilled in the art. For example, features recited in the various dependent claims could be combined with each other in any suitable combination(s). In addition, features from different embodiments described above could be selectively combined into a new embodiment. Accordingly, the description is intended to embrace all such alternatives, modifications and variances which fall within the scope of the appended claims.

What is claimed is:

1. An apparatus comprising:
   a debrider that includes:
      a shaft;
      an outer blade located at a distal end of the shaft;
      an electrical insulator band located around and directly abutting the outer blade;
      an electrically conductive band located around and directly abutting the electrical insulator;
      an electrical insulator sheath covering the shaft and a portion of the outer blade, the sheath including:
         an elongated hollow tube having a wall; and
         at least one electrical lead embedded inside the wall; and
      a leg including a strip extending between the electrically conductive band and a portion of the electrical insulator sheath, wherein the at least one electrical lead is configured to electrically couple with the electrically conductive band via the leg.

2. The apparatus as in claim 1, wherein the at least one electrical lead comprises a single electrical lead along a length of the tube.

3. The apparatus as in claim 1, wherein the at least one electrical lead comprises two electrical leads extending along a length of the tube.

4. The apparatus as in claim 1, wherein a distal portion of the sheath is flexible in a semi-rigid fashion including the wall and the at least one electrical lead is bendable at the distal portion.

5. The apparatus as in claim 1, wherein the tube is formed by extruding the tube onto the at least one electrical lead to form the at least one electrical lead embedded inside the wall.

6. The apparatus as in claim 1, wherein opposite ends of the at least one electrical lead are exposed at opposite ends of the tube.

7. The apparatus as in claim 1 wherein the debrider is mechanically connected to a distal end of the tube and the debrider comprises an electrically conductive member which is electrically connected to a distal end of the at least one electrical lead.

8. The apparatus as in claim 7 further comprising an electrically insulating member located over a connection of the electrically conductive member to the distal end of the at least one electrical lead.

9. The apparatus as in claim 7, wherein the electrically conductive member comprises a portion of a bipolar trace for bipolar coagulation.

10. The apparatus as in claim 9, wherein the debrider includes an inner blade that extends through the sheath.

11. The apparatus of claim 1, wherein the sheath is polymeric and the polymeric sheath and the at least one electrical lead are configured to provide radiofrequency (RF) energy for a surgical operation when the polymeric sheath is connected to a RF energy source.

12. The apparatus of claim 11, wherein the polymeric sheath comprises at least one electrical lead.

13. The apparatus as in claim 1, wherein the leg extends away from a distal end of the outer blade towards the sheath.

14. The apparatus as in claim 1, wherein the shaft includes a flexible section and the flexible section is covered by the sheath and wherein the leg is located more distal than the flexible section.

* * * * *

UNITED STATES PATENT AND TRADEMARK OFFICE
CERTIFICATE OF CORRECTION

PATENT NO. : 11,766,288 B2  
APPLICATION NO. : 16/282760  
DATED : September 26, 2023  
INVENTOR(S) : Alsaffar et al.

Page 1 of 1

It is certified that error appears in the above-identified patent and that said Letters Patent is hereby corrected as shown below:

On the Title Page

On page 2, in Column 2, item (56) under "Other Publications", Line 27, delete ""Hightlights" and insert --"Highlights-- therefor Signed and Sealed this  
Twenty-eighth Day of January, 2025

Coke Morgan Stewart  
*Acting Director of the United States Patent and Trademark Office*